US008287898B2

(12) United States Patent
Jandacek et al.

(10) Patent No.: US 8,287,898 B2
(45) Date of Patent: *Oct. 16, 2012

(54) COMPOSITIONS AND METHODS FOR BODY WEIGHT MANAGEMENT

(75) Inventors: Ronald James Jandacek, Cincinnati, OH (US); Gary Robert Kelm, Cincinnati, OH (US); Satinder Singh Bharaj, Liberty Township, OH (US); Jorge Villanueva Penafiel, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 957 days.

This patent is subject to a terminal disclaimer.

(21) Appl. No.: 11/120,853

(22) Filed: May 3, 2005

(65) Prior Publication Data
US 2005/0197395 A1 Sep. 8, 2005

Related U.S. Application Data

(63) Continuation of application No. 09/603,626, filed on Jun. 26, 2000, now Pat. No. 7,025,984.

(51) Int. Cl.
A61K 9/00 (2006.01)
A61K 9/48 (2006.01)
A61K 9/20 (2006.01)
A61K 47/00 (2006.01)

(52) U.S. Cl. ......... 424/439; 424/400; 424/451; 424/464

(58) Field of Classification Search .................. 424/400, 424/439, 451, 464
See application file for complete search history.

(56) References Cited

U.S. PATENT DOCUMENTS

| | | | |
|---|---|---|---|
| 4,237,118 A | 12/1980 | Howard et al. | |
| 4,298,601 A | 11/1981 | Howard | |
| 4,900,566 A * | 2/1990 | Howard | 426/72 |
| 5,068,119 A | 11/1991 | Klemann et al. | |
| 5,322,697 A | 6/1994 | Meyer | |
| 5,589,508 A | 12/1996 | Schlotzer et al. | |
| 5,665,384 A | 9/1997 | Courteille et al. | |
| 5,674,896 A | 10/1997 | Yoshida et al. | |
| 5,753,253 A | 5/1998 | Meyer | |
| 5,977,175 A | 11/1999 | Lin et al. | |
| 5,977,195 A | 11/1999 | Craig et al. | |
| 6,034,132 A | 3/2000 | Remmereit | |
| 6,207,638 B1 | 3/2001 | Portman | |
| 6,210,702 B1 | 4/2001 | Samman | |
| 6,225,486 B1 | 5/2001 | Saebo et al. | |
| 6,267,988 B1 * | 7/2001 | Meyer | 424/489 |
| 6,429,190 B1 | 8/2002 | Portman | |
| 6,517,883 B1 * | 2/2003 | Herslof et al. | 426/602 |
| 6,953,583 B1 | 10/2005 | Ghisalberti | |
| 7,025,984 B1 * | 4/2006 | Jandacek et al. | 424/439 |
| 2002/0081711 A1 | 6/2002 | Herlyn et al. | |

FOREIGN PATENT DOCUMENTS

| | | |
|---|---|---|
| EP | 0003407 A1 | 8/1979 |
| EP | 0003407 B1 | 8/1979 |
| EP | 0771817 A2 | 5/1997 |
| EP | 0954975 A2 | 11/1999 |
| GB | 2355382 A | 4/2001 |
| WO | WO 87/03198 A1 | 6/1987 |
| WO | WO 99/13739 | 3/1999 |
| WO | WO 99/56781 | 11/1999 |
| WO | WO 01/17374 A1 | 3/2001 |

OTHER PUBLICATIONS

Ramirez et al, Satiety from Fat ? Adverse Effects of Intestinal Infusion of Sodium Oleate, 1997, 273(5, part 2), R1779-1785.*
Saghir et al, Rapid in vivo hydrolysis of fatty acid ethyl esters, toxic nonoxidative ethanol metabolites, 1997, American Journal of Physiology, 273 (1, pt.1), G184-G190 (abstract p. 1 ).*
Cox et al., "Suppression of food intake, body weight, and body fat by jejunal fatty acid infusions", Am. J. Physiology, Regulatory Integrative Comparative Physiology, vol. 278, pp. R604-R610, 2000.
Friedman et al., "Fatty Acid Oxidation Affects Food Intake by Altering Hepatic Energy Status," Am. J. Physiology, vol. 276, pp. R1046-R1053, 1999.
Greenberg et al., "Intravenous triglycerides fail to elicit satiety in sham-feeding rats", The American Physiological Soceity, vol. 264, pp. R409-R413, 1993.
Greenberg et al., "Intraduodenal infusions of fats elicit satiety in sham-feeding rats," Am. J. Physiology, vol. 259, pp. R110-R118, 1990.
Greenberg et al., "Fats and Satiety: The Role of the Small Intestine," Appetite, vol. 31, p. 229, 1998.
Greenberg, " ", Intestinal Satiety, lin Satiation from Gut to Brain, G. P. Smith (ed.), pp. 40-70, Oxford U. Press, Inc., NY, INY, 1998.
Kahler et al., "Suppression of Hepatic Fatty Acid Oxidation and Food Intake in Men," Nutrition, vol. 15, pp. 819-828, 1999.
Langhans et al., "Role of Fatty Acid Oxidation in Control of Meal Pattern," Behavioral and Neural Biology, vol. 47, pp. 7-16, 1987.
Langhans et al., "Evidence for a Vagally Mediated Satiety Signal Derived from Hepatic Fatty Acid Oxidation," J. of Autonomic Nervous System, vol. 18, pp. 13-18, 1987.
Meyer et al. "Role of Small Intestine in Caloric Compensations to Oil Premeals in Rats," Am. J. Physiology, vol. 275, pp. R7-R14, 1995.
Meyer et al., "Chemical Specificites and Intestinal Distributions of Nutrient-Driven Satiety," Am. J. Physiology, vol. 275, pp. R1293-R1307, 1998.
Meyer et al., "Length of Intestinal Contact on Nutrient-Driven Satiety," Am. J. Physiology, vol. 275, pp. R1293-R1307, 1998.

(Continued)

Primary Examiner — Taylor Victor Oh
(74) Attorney, Agent, or Firm — Amy M. Foust; Kelly L. McDow; Adam W. Borgman

(57) ABSTRACT

The present invention is for compositions and methods for managing the body weight of a subject using said compositions. Weight management, particularly weight gain and loss, is effectuated by producing a sensation of satiety in said subjects. The method of managing body weight includes administering the composition prior to food consumption, concurrent with food consumption, as replacement for food consumption and combinations thereof.

21 Claims, No Drawings

OTHER PUBLICATIONS

Rolls et al., "Time Course of Effects of Preloads High in Fat or Carbohydrate on Food Intake and Hunger Ratings in Humans," *Am. J. Physiology*, vol. 260, pp. R756-R763, 1991.

Welch et al., "Comparisons of the Effects on Satiety and Eating Behaviour of Infusion of Lipid into the Different Regions of the Small Intestine," *Gut.*, vol. 29, pp. 306-311, 1988.

Welch et al., "Effect of Ileai and Intravenous Infusions of Fat Emulsions on Feeding and Satiety in Human Volunteers," *Gastroenterology*, vol. 89, pp. 1293-1297, 1985.

Woltman et al., "Role of Cholecystokinin in the Anorexia Produced by Duodenal Delivery of Oleic Acid in Rats," *Am. J. Physiology*, vol. 269, pp. R1420-R1433, 1995.

Woltman et al., "Effects of Duodenal and Distal Ileal Infusions of Glucose and Oleic Acid on Meal Patterns in Rats," *Am. J. Physiology*, vol. 269, pp. R7-R14, 1995.

Saghir, M., et al., Rapid in vivo hydrolysis of fatty acid ethyl esters, toxic nonoxidative ethanol metabolites, Americal Journal of Physiology—Gastrointestinal and Liver Physiology, 273(1):G184-G190, 1997 (full text).

\* cited by examiner

COMPOSITIONS AND METHODS FOR BODY WEIGHT MANAGEMENT

CROSS REFERENCE TO RELATED APPLICATION

This application is a continuation application of prior U.S. application Ser. No. 09/603,626 filed Jun. 26, 2000 now U.S. Pat. No. 7,025,984.

BACKGROUND OF THE INVENTION

The incidence of obesity in the general population of the United States has shown a dramatic increase over the last decade with over 50% of the population considered overweight or obese. A similar trend is observed in other countries as the so-called Western diet is adopted. Since obesity is associated with a variety of co-morbidities such as diabetes, hypertension, and atherosclerosis, this increase is a major health concern.

A number of approaches have been proposed or used to help subjects reduce food intake, otherwise referred to as energy intake, and thereby manage their body weight. These approaches include use of agents to act on the central nervous system to increase levels of serotonin, and those acting in the gastrointestinal tract to reduce digestion and/or absorption of nutrients. These approaches suffer from potential side effects that reduce their utility for long-term body weight management.

A different approach involves the introduction of nutrients directly into the distal small intestine in an attempt to reduce concomitant food intake. This approach uses natural materials and is believed to function via interactions of the nutrients with putative receptors throughout the small intestine, particularly in the distal small intestine (jejunum, ileum) that are believed to participate in the natural mechanisms that induce termination of a meal. This offers the potential advantage of a reduction of side effects due to the use of natural materials and mechanism. Reported data in animals and humans are based on using catheters and naso-gastric tubes respectively, to directly introduce nutrients into their small intestines. Many of the reported studies have employed lipids. For example, infusion of a corn oil emulsion into the small intestine (jejunum or ileum) reduces food intake at a concomitant meal such that total caloric intake (meal plus infusate) is significantly or directionally reduced; see I. Welch, K. Saunders and N. W. Read, *Effect of Ileal and Intravenous Infusions of Fat Emulsions on Feeding and Satiety in Human Volunteers*, Gastroenterology 89: 1293-1297, 1985; I. Welch, C. P. Sepple and N. W. Read, *Comparisons of the Effects on Satiety and Eating Behavior of Infusion of Lipid into the Different Regions of the Small Intestine*, Gut 29: 306-311, 1988; all incorporated herein by reference. Intravenous administration of a triacylglycerol emulsion (Intralipid) failed to reduce total caloric intake in several studies; see I. Welch, K. Saunders and N. W. Read, id.; E. K. Walls and H. S. Koopmans, *Effect of Intravenous Nutrient Infusions on Food Intake in Rats*, Physiiology & Behavior 45: 1223-1226, 1989; all incorporated herein by reference. Pre-meals of triacylglycerol in yogurt also fail to reduce total caloric intake (meal plus pre-meal) at a subsequent meal; see B. J. Rolls, S. Kim, A. L. McNelis, M. W. Fischman, R. W. Foltin, and T. H. Moran, *Time Course of Effects of Preloads High in Fat or Carbohydrate on Food Intake and Hunger Ratings in Humans*, Am. Journl. Physiology, 260: R756-R763, 1991; J. H. Meyer, M. Hlinka, A. Khatibi and H. E. Raybould, *Role of Small Intestine in Caloric Compensations to Oil Premeals in Rats*, Am. Journl. Physiology, 275: R1320-R1333, 1998; all incorporated herein by reference.

There are many animal studies where nutrients are infused into the small intestine to reduce food intake. For example, Woltman et al. have shown that micellar solutions of oleate infused into the duodenum reduced 4-hour food intake in rats to a greater extent than a micellar triolein solution and that duodenal infusion is more potent than ileal infusion in reducing food intake; see T. Woltman and R. Reidelberger, *Effects of Duodenal and Distal Ileal Infusions of Glucose and Oleic Acid on Meal Patterns in Rats*, Am. Journl. Physiology, 269: R7-R14, 1995; T. Woltman, D. Castellanos and R. Reidelberger, *Role of Cholecystokinin in the Anorexia Produced by Duodenal Delivery of Oleic Acid in Rats*, Am. Journl. Physiology, 269 R1420-R1433, 1995; all incorporated herein by reference. Greenberg et al have shown that duodenally infused emulsions of triacylglycerol and linoleic acid reduce total caloric intake in a sham feeding rat model, whereas ileal infusions do not; see D. Greenberg, G. P. Smith and J. Gibbs, *Intraduodenal Infusions of Fats Elicit Satiety in Sham Feeding Rats*, Am. Journl. Physiology, 259: R110-R118, 1990; D. Greenberg, G. P. Smith and J. Gibbs, *Intravenous Triglycerdies Fail to Elicit Satiety in Sham-Feeding Rats* Am. Journl. Physiology, 264: R409-R413, 1993; D. Greenberg, *Fats and Satiety: the Role of the Small Intestine*, Appetite 31: 229, 1998; D. Greenberg, *Intestinal Satiety, in Satiation from Gut to Brain*, G. P. Smith (ed.), pp. 40-70, Oxford University Press, Inc., New York, N.Y., 1998; all incorporated herein by reference. Other long chain fatty acids (oleic, linolenic) were somewhat less effective.

Meyer et al. have conducted a series of studies investigating the effects of infused nutrients upon total caloric intake in rats constrained to three hours of feeding. They found that emulsions of fatty acids greater than 10 carbons in length, solutions of monomeric carbohydrates only with affinity for the glucose transporter, and solutions of the amino acids tryptophan and phenylalanine suppressed total caloric intake when infused in the duodenum or mid-gut (jejunum), or into the colon. These investigators also demonstrated that pre-meals of triacylglycerol failed to suppress total caloric intake in rats constrained to seven hours of feeding; see J. H. Meyer, M. Hlinka, Y. Tabrizi, N. DiMaso and H. E. Raybould, *Chemical Specificities and Intestinal Distributions of Nutrient-Driven Satiety*, Am. Journl. Physiology, 275: R1293-R1307, 1998; J. H. Meyer, Y. Tabrizi, N. DiMaso, M. Hlinka and H. E. Raybould, *Length of Intestinal Contact on Nutrient-Driven Satiety*, Journl. Physiology, 275: R1308-R1319, 1998; all incorporated herein by reference.

More recently, Cox et al. have shown that jejunally infused neat linoleic acid or oleic acid (0.2 mL/hr for seven hours) will significantly reduce total daily caloric intake in rats, whereas a long chain triacylglycerol (corn oil) will not. These authors also demonstrated that the reduction is maintained over 20 days of dosing, resulting in a significant difference in weight between treated and control animals; see J. E. Cox, W. J. Tyler, A. Randich, G. R. Kelm, S. S. Bharaj, R. J. Jandacek and S. T. Meller, *Suppression of Food Intake, Body Weight, and Body Fat by Jejunal Fatty Acid Infusions*, Am. Jourl. Physiology, Regulatory Integrative Comparative Physiology, 278: R604-R610, 2000; all incorporated herein by reference.

There are no reported studies known to the inventors in which ingested or gastrically administered nutrients in a pharmaceutical dosage form designed to release the nutrients in the small intestine have been used to reduce food intake. PCT Application WO 87/03198, U.S. Pat. Nos. 5,322,697, and 5,753,253 disclose using such pharmaceutical preparations for reduction of food intake; all incorporated herein by reference. Infusion data are provided to support these disclosures However, no data are provided that are derived from the use of enteric nutrient dosage forms designed to release in the small intestine for reducing food consumption and total caloric intake.

Body weight management methods employing natural nutrients to reduce food intake through natural mechanisms are highly sought after. A need still exists for a product comprising nutrient materials that can be ingested by human and animal subjects to reduce consumption of food and lower the total daily caloric intake of the subject

BRIEF DESCRIPTION OF THE INVENTION

The present invention is for compositions, and methods for managing body weight of human and animal subjects using said compositions. The compositions of the present invention comprise satiety agents selected from the group consisting of long chain fatty acids, their non-glyceryl esters, hydrolyzable in the presence of gastro-intestinal enzymes, and mixtures thereof, wherein said satiety agent releases in the stomach. The compositions are administered prior to food consumption, concurrent with food consumption, as replacement for food consumption and combinations thereof. Consuming compositions of the present invention produces a sensation of satiety in the subjects for a sufficient time wherein the amount of food subsequently consumed is regulated by controlling the subject's appetite.

One objective of the present invention is to provide a safe and effective composition that promotes body weight management of subjects consuming the compositions of the present invention. Said management of body weight can be combined with currently used regimens of diet and exercise for both humans and animals. Another objective is to provide a method for controlling appetite comprising administration of a composition comprising a satiety agent.

DETAILED DESCRIPTION OF THE INVENTION

The underlying principle of the present invention is the recognition that ingestion of compositions comprising long chain non-esterified fatty acids, or the non-glyceryl esters thereof have the potential to increase hepatic mitochondrial oxidation due to portal absorption of long chain non-esterified fatty acids as such. This may be due to a reduction in the lumenal levels of 2-monoacylglycerol derived from lumenal hydrolysis of triacylglycerol. While not wishing to bound by theory, the inventors believe that appetite control is achieved when there is rapid onset and increased rate of hepatic mitochondrial oxidation of long chain non-esterified fatty acids provided by a compositions of the present invention relative to oxidation of long chain non-esterified fatty acids derived from triacylglycerol that are the primary source of fatty acids in the diet. Appetite control is a primary factor in managing the body weight of subjects.

Hepatic mitochondrial long chain non-esterified fatty acid oxidation rate is, therefore, considered to be an important factor for controlling food intake. For example, rat and human administration of long chain non-esterified fatty acid oxidation inhibitors produce an increase in food intake. This effect is ameliorated by hepatic vagotomy demonstrating that the liver is an important component in this control; see W. Langhans and E. Scharrer, *Role of Fatty Acid Oxidation in Control of Meal Pattern*, Behavioral and Neural Biology 47: 7-16, 1987; M. L Friedman, R. B. Harris, H. Ji, I Ramierez and M. G. Tordorr, *Fatty Acid Oxidation Affects Food Intake by Altering Hepatic Energy Status*, Am. Journl. Physiology, 276: R1046-R1053, 1999; A. Kahler, M. Zimmermann and W. Langhans, *Suppression of Hepatic Fatty Acid Oxidation and Food Intake in Men*, Nutrition 15: 819-828, 1999; W. Langhans and E. Scharrer, *Evidence for a Vagally Mediated Satiety Signal Derived from Hepatic Fatty Acid Oxidation*, J. Autonomic Nervous System 18: 13-18, 1987; all incorporated herein by reference. Thus, it appears that the body attempts to maintain relatively constant levels of long chain non-esterified fatty acids in the blood and that these levels are monitored by the rate of hepatic mitochondrial long chain non-esterified fatty acid oxidation which is transmitted to the brain by vagal afferents. Decreases in hepatic mitochondrial long chain non-esterified fatty acid oxidation lead to increased food intake, whereas increases lead to a reduction in food intake. Therefore, a composition increasing the rate and extent of hepatic mitochondrial long chain non-esterified fatty acid oxidation will lead to a reduction in food intake and facilitate management of a subject's body weight.

Essentially all long chain fatty acids in the diet are ingested in the form of triacylglycerols. Triacylglycerols are hydrolyzed to long chain non-esterified fatty acids and 2-monoacylglycerols in the lumen of the small intestine. However, the resulting long chain non-esterified fatty acids and 2-monoacylglycerols are re-esterified into triacylglycerols in the enterocytes and formed into small emulsion droplets stabilized by lipoproteins that are termed chylomicrons. Upon exocytosis from the enterocytes, the chylomicrons partition into the lymph vessels instead of the portal vein. Most other nutrients and xenobiotics are absorbed through the portal vein and pass quantitatively through the liver before distribution to the rest of the body. However, since the lymph vessels empty into the blood circulation subsequent to the liver, ingested fatty acids from triacylglycerols are first distributed throughout the body in the form of triacylglycerols. Little of these reach the liver in the form of long chain non-esterified fatty acids during the course of a meal and thus influence food intake.

It is believed that a portion of the long chain non-esterified fatty acids provided by compositions of the present invention is absorbed through the portal vein as long chain non-esterified fatty acids due to a reduction of 2-monoacylglycerols in the lumen of the small intestine. The reduction in 2-monoacylglycerol levels is believed to reduce re-esterification of long chain non-esterified fatty acids in the enterocytes and permit some of the absorbed long chain non-esterified fatty acids to exit the basolateral side of the enterocytes prior to being re-esterified to triacylglycerols and formed into chylomicrons. The long chain non-esterified fatty acids that basolaterally exits the enterocyte as such can partition into the portal vein and thus reach the liver in an oxidizible state quantitatively. This has the potential to greatly increase the rate of hepatic mitochondrial long chain non-esterified fatty acids oxidation relative to a similar amount of fatty acid ingested in the form of a triacylglycerols.

Since distal release of the long chain non-esterified fatty acids is not required in the present invention, there is no need to prepare elaborate enteric dosage forms designed to release the long chain non-esterified fatty acids in the distal small intestine. Thus, the present invention represents a significant improvement over the prior art, which indeed does not contain data demonstrating food intake reduction from such putative enteric dosage forms.

Therefore, the present invention is for compositions, methods of using said compositions and methods for managing the body weight of a subject using said compositions. Body weight control, particularly weight gain and loss is effectuated by producing a sensation of satiety in said subjects consuming compositions of this invention.

The oral composition of the present invention comprise satiety agents selected from the group consisting of long chain fatty acids, their non-glyceryl esters, hydrolyzable in the presence of gastrointestinal enzymes, and mixtures thereof wherein said satiety agent releases in the stomach. Consuming compositions of the present invention induce a sensation of satiety in the subjects for a sufficient time wherein the amount of food subsequently consumed is regulated by controlling the subject's appetite.

Satiety Agents

It has been surprisingly discovered that administration of a satiety agent selected from the group consisting of long chain (greater than 10 carbons) non-esterified fatty acids, their non-glyceryl esters, hydrolyzable in the presence of gastro-intestinal enzymes, and mixtures thereof in compositions that release said satiety agent in the stomach reduces total caloric intake. This satiety agent may be administered in a wide variety of product forms including non-enteric pharmaceutical dosage forms such as compressed and molded tablets, hard gelatin capsules, soft elastic gelatin capsules, and microcapsules that dissolve in the stomach, emulsions, and suspensions, or as part of a beverage or solid food product. The latter may be used as a meal supplement or replacement. The compositions are administered at a time prior to subsequent consumption of food so as to induce a sensation of satiety in the subjects for a sufficient time wherein the amount of food subsequently consumed is reduced, thus reducing total caloric intake by controlling the subject's appetite. This is believed to be an effective body weight management tool.

The compositions of the present invention comprise satiety agents selected from the group consisting of long chain fatty acids, their non-glyceryl esters, hydrolyzable in the presence of gastro-intestinal enzymes, and mixtures thereof, wherein said satiety agent releases in the stomach. The long chain fatty acids and their non-glyceryl esters contain from about 12 to about 24, preferably from about 16 to about 18 carbon atoms. The carbon chain has from 0 to about 6, preferably from 0 to about 3 carbon-carbon atom double bonds. The fatty acids are selected from group consisting of lauric acid, lauroleic acid, myristic acid, myristoleic acid, pentadecanoic acid, palmitic acid, palmitoleic acid, margaric acid, stearic acid, dihydroxystearic acid, oleic acid, ricinoleic acid, elaidic acid, linoleic acid, alpha-linolenic acid, dihomogamma-linolenic acid, eleostearic acid, licanic acid, arachidonic acid, arachidic acid, eicosenoic acid, eicosapentaenoic acid, behenic acid, erucic acid, docosahexaenoic acid, lignoceric acid and mixtures thereof. Preferred fatty acids are selected from the group consisting of oleic acid, linoleic acid and mixtures thereof.

Non-glyceryl fatty acid esters include, but, are not limited to alcohol esters wherein said alcohol portion of the ester is selected from the group of alcohols consisting of methanol, ethanol, n-propanol, isopropanol, n-butanol, isobutanol and mixtures thereof, preferably ethanol. Preferred non-glyceryl fatty acid esters are selected from the group consisting of ethyl oleate, ethyl linoleate and mixtures thereof.

Method of Body Weight Management

The composition according to the present invention is administered to an animal or human subject at a level of said satiety agent is from about 0.01 grams per kilogram body weight to about 10.0 grams per kilogram body weight, preferably from about 0.04 grams per kilogram body weight to about 1.0 grams per kilogram body weight per serving of said composition to said subject. Animal subjects include, but, are not limited to companion animals such as dogs, cats, horses or other similar animals. The term serving refers to the amount of composition that is typically consumed at a given time wherein the composition may be in any number of food forms including liquid beverages such as milk shakes, fruit juices or the like, solid food products such as bars, or pharmaceutical dosage forms including compressed and molded tablets, soft and hard gelatin capsules, microcapsules, emulsions, and suspensions. It is preferable wherein said methods are employed in a daily routine over the entire course of a designed or planned weight management program The methods for managing the body weight of humans and other animal subjects using compositions of the present invention comprise the step of administration of said composition to the subject at a time prior to food consumption, during food consumption, as a replacement for food consumption and combinations thereof. When taken during food consumption, the composition of the present invention can be taken separately with the food or can processed into making a food comprising said composition. Any food consumed or processed with said invention preferably has a maximum triacylglycerol level of about 5 grams. When administered prior to food consumption, the period prior to consumption of food is sufficiently early enough to prevent substantial interaction with any triacylglycerol components of the food being consumed and to increase hepatic fatty acid β-oxidation and hepatic and celiac vagal activity during said consumption, leading to premature induction of satiety and reduction of energy intake during consumption. Said composition is also believed to be effective in a method for controlling the appetite of a subject.

Generally, administration of the composition of the present invention takes place from about 30 minutes to 6 hours prior to consumption of food. It is preferable that the composition be taken in this period, prior to the subject's primary meals of the day, usually before their morning, mid-day and evening meals.

Administration of the composition of the present invention may also replace one or a plurality of the said subject's primary meal or meals.

Additional Ingredients

As previously stated the composition can be made in a plurality of convenient product forms. In this regard, a number of additional ingredients are used in the product formulations to develop a commercially acceptable product such as those previously mentioned herein. One particular favored product form for consumption by humans is a thick, frothy beverage having the consistency of a milk shake. Various optional ingredients used to make such a product include suspending agents, flavorants and viscosity modifiers. Other particular product forms include pharmaceutical dosage forms such as tablets. Optional ingredients for tablets include, but are not limited to diluents such as microcrystalline cellulose, absorbants such as colloidal silicon dioxide, disintegrants such as croscarmellose sodium and crospovidone, binders such as povidone, surfactants such as polyoxyethylene alkyl ethers, polyoxyethylene castor oil derivatives, polyoxyethylene sorbitan fatty acid esters, and glyceryl and multiglyceryl fatty acid esters (that do not form 2-monoacylglycerols), and flavors and sweeteners, all at levels appropriate to formulation of suitable tablets that may be compressed using commercial machinery or molded based upon the physical/chemical properties of the selected satiety agent or agents. Hard gelatin capsules may include any of the optional ingredients listed for tablets that may be required to prepare a suitable mass for filling into hard gelatin using commercial machinery. Soft elastic gelatin capsules contain optional ingredients that most typically will include surfactants such as polyoxyethylene alkyl ethers, polyoxyethylene castor oil derivatives, polyoxyethylene sorbitan fatty acid esters, and glyceryl and multiglyceryl fatty acid esters (that do not form 2-monoacylglycerols). In addition to surfactants, optional ingredients in emulsions and suspensions may include hydrocolloids such as methylcellulose, hydroxypropyl methylcellulose, xanthan gum, and guar gum, and flavors and sweeteners.

EXAMPLES

The following are non-limiting examples of the present compositions which are processed using conventional methods. Such examples of the products are used taken or delivered in a serving or dose that preferably is consumed in its entirety at a time prior to, concomitant with or in place of the consumption of food. The following examples are provided to illustrate the invention and are not intended to limit the scope thereof in any manner:

Ready-To-Drink Beverage

| Ingredients | Example I (% w/v) | Example II (% w/v) | Example III (% w/v) |
|---|---|---|---|
| Mineral Salts | 0.0062 | 0.0062 | 0.0062 |
| Sodium Hydroxide* | 0.0175 | 0.0175 | 0.0175 |
| Carageenan[1] | 0.0350 | 0.0350 | 0.0350 |
| Cellulose gel[2] | 0.5200 | 0.5200 | 0.5200 |
| Gum Arabic Low Viscosity | 0.4100 | 0.4100 | 0.4100 |
| Vitamin/Mineral Blend[3] | 0.4340 | 0.4340 | 0.4340 |
| Lecithin[4] | 0.0261 | 0.0261 | 0.0261 |
| Mono & Diglycerides[5] | 0.0400 | 0.0400 | 0.0400 |
| Ethyl Oleate[6] | 1.0811 | 2.1505 | 3.2432 |
| Cocoa[7] | 1.2000 | 1.2000 | 1.200 |
| AF Emulsion Antifoam* | 0.0020 | 0.0020 | 0.0020 |
| Sodium Caseinate[8] | 0.2990 | 0.2990 | 0.2990 |
| High Heat Nonfat Dry Milk | 6.8000 | 6.8000 | 6.8000 |
| Maltodextrin[9] | 2.4320 | — | — |
| Granulated Sugar | 3.9500 | 3.9500 | 3.9500 |
| Sucralose Liquid | 0.0539 | 0.0587 | 0.0587 |
| Vanilla Flavor[10] | 0.0015 | 0.0015 | 0.0015 |
| Cream Flavor[11] | 0.0015 | 0.0015 | 0.0015 |
| Vanilla Flavor[12] | 0.1000 | 0.1000 | 0.1000 |
| QS Water | | | |
| Total | 100.00 | 100.00 | 100.00 |

*Process aids. Use as needed, up to about level indicated
[1]SeaKem CM611 and Viscarin SD389 both from FMC
[2]Avicel CL-611 from FMC
[3]FT-001106 available from Fortitech
[4]Centrolex-F available from Central Soya Company, Inc.
[5]Myvatex 8-06 available from Quest International USA, Inc.
[6]05--58405 available from Penta Manufacturing Co., or Crodamol EO from Croda Inc.
[7]DeZaan D-11-A available from ADM
[8]Available from DMV International
[9]Maltodextrin 10 DE (M-100) available from Grain Processing Corporation
[10]Flavor #14896 available from David Michael and Co., Inc.
[11]Flavor #1967 available from David Michael and Co., Inc.
[12]Flavor VA03 available from Virginia Dare Extract Co., Inc.

Method of Preparation:

Add approximately 90% of the required water to a batch processor and heat to 130-140° F. Add flavors to the storage tank. Recirculate initial water through a liquifier maintaining a level in the liquifier between ½ and ⅔ full. Add all ingredients except the flavorings to the liquifier in the order listed above. Add the mono & diglycerides prior to the addition of ethyl oleate. Add the emulsion antifoam prior to sodium caseinate and nonfat dry milk. Stop the flow to the liquifier. Empty the liquifier and flush with 20 pre-measured gallons of water. Route the product from the processor through the heat exchanger, homogenizer, and back through the heat exchanger to the processor. Heat to 170° F. (±5° F.), homogenize at 4500 psi total, 500 psi second stage and cool to less than 45° F. After establishing temperature and pressure for 4 minutes and 30 seconds, divert the flow to the storage tank.

When the product level gets down to one foot in cone bottom processor, put processor in circulation for 4 minutes and 30 seconds to ensure complete homogenization. Take the homogenizer pressure off. Turn the heat off and flush the system with pre-measured water to 95% total batch weight. Mix for twenty (20) minutes before pulling samples for standardizing. After standardizing has been completed (total desired solids) QS with water.

The beverage is sent to package equipment where it filled in the appropriate package. The packaging of these beverages can either be retort or aseptically sterilized. The desired metal beverage cans, such as a DWI Tinplate food can (300×315 with 18 beads for a 12 oz. serving) would be used for a retort process. A "Dole" type metal can would be used as an example for an aseptic process.

Example IV

Confectionery Bar

| Material | % w/w |
|---|---|
| High Fructose Corn Syrup | 18.0 |
| Honey-Clover | 18.0 |
| Defatted Peanut Flour | 5.0 |
| Isolated Soy Protein Isolate[1] | 28.2 |
| Nonfat Dry Milk[2] | 10.0 |
| Brown Sugar | 6.0 |
| Ethyl Oleate[3] | 14.0 |
| Natural Orange[4] | 0.2 |
| Fatty Acid Masker[5] | 0.1 |
| Natural Peanut Flavor[6] | 0.1 |
| Natural Honey Flavor[7] | 0.1 |
| Vanilla Custard Flavor[8] | 0.1 |
| Soy Lecithin[9] | 0.2 |
| Total | 100.0 |

[1]Supro 661 available from Protein Technologies International
[2]Low Heat type available from Agrimark
[3]Crodamol EO available from Croda, Inc., or 05-58405 from Penta Manufacturing Co.
[4]Flavor 57.458/AP SD available from Firmenich
[5]Flavor 348118 available from Firmenich
[6]Flavor 57.304/T available from Firmenich
[7]Flavor 598.513/8 available from Firmenich
[8]Flavor HC600-137 available from P&G
[9]Alcolec S available from American Lecithin Company Method of Preparation:

Weigh and pre-blend all powdered materials in a suitable mixer/blender. Weigh and blend the high fructose corn syrup and honey in a suitable size vessel. Heat the syrup blend to about 90° F. Weigh the ethyl oleate in a suitable size vessel. Weigh and add all the liquid flavors and the soy lecithin to the ethyl oleate: Mix until uniform. To an appropriate size mixer (e.g., Hobart, sigma blade mixer), add the powdered blend, ethyl oleate blend and syrups together. Mix/knead until a uniform texture results.

Slab the batch and cut into bar cores about 57 grams by weight (approximately 1½" width, ½" height, 3½" length). Coat or enrobe the bar cores with a milk chocolate or other such desired coating mixture. Cool the coated bars to room temperature before packaging. Each bar contains about 8 grams of ethyl oleate.

Example V

Molded Tablet

Melt palmitic acid and polyoxyl 40 hydrogenated castor oil and combine in a ratio of 4:1 respectively. Pour the combination or melt into appropriately sized tablet molds wherein each tablet contains about 0.5 g palmitic acid. Cool the molds until solidified and remove tablets from the molds.

Example VI

Soft Gelatin Capsule

Encapsulated neat linoleic acid (technical grade) in a #20 oblong soft gelatin capsule using the standard soft-gelatin ribbon/die process such that each capsule contains about 1 gram of the linoleic acid.

Example VII

Hard Gelatin Capsule

Combine oleic acid (90%) and flumed silica in a ratio of 1:1 using a high shear mixer. Encapsulate the resulting mixture into Size 00 hard gelatin capsules using standard high speed capsule filling machine such that each capsule contains about 0.4 grams of oleic acid.

Example VIII

Pharmaceutical Emulsion

| Component | Wt. Pct. |
|---|---|
| Ethyl Oleate | 20.0 |
| Triglyceryl Monooleate | 3.0 |
| Polysorbate 80 | 2.0 |
| Flavor | 0.5 |
| Sodium Saccharin | 0.2 |
| Purified Water | q.s |
| Total | 100.0 |

Method of Preparation:

Disperse triglyceryl monooleate into ethyl oleate. Dissolve polysorbate 80 into purified water. Emulsify the oil and water solutions using a Microfluidizer (Microfluidics Corp.). Add flavor and sodium saccharin with additional agitation. The emulsion product is packaged into liquid containing packaging such as 500 ml amber glass bottles.

Example IX

Microcapsules

| Component | Wt. Pct. |
|---|---|
| Gelatin[1] | 33.0 |
| Hexameta Polyphosphate | 3.0 |
| Eicosapentaenoic acid | 59.9 |
| Glutaraldehyde | 4.1 |

1 Type A, 275 Bloom available from Knox Gelatin Co.

Method of Preparation:

Dissolve gelatin in about 150 g of purified water at about 55° C. Dissolve the hexameta polyphosphate in 20 g purified water at about 55° C. Emulsify the eicosapentaenoic acid into the gelatin solution under a nitrogen blanket at about 450 rpm. Add about 120 g purified water at about 55° C. to the emulsion, maintaining agitation at about 450 rpm. Add the polyphosphate solution to the emulsion. Adjust the pH of the resulting mixture to between 3.5 and 4.5 with glacial acetic acid. Remove heat and allow the mixture to cool slowly to room temperature with continued agitation. Additionally cool the mixture to about 10° C. Add glutaraldehyde and allow cross-linking reaction to occur overnight. Wash resulting microcapsules three times with purified water and filter dry. Package said microcapsules into appropriate packaging such as small volume plastic pharmaceutical vials.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for managing the body weight of humans and other animal subjects comprising the step of administering to said subjects an oral composition comprising ethyl oleate, wherein said ethyl oleate releases in the stomach; and wherein the oral composition is in a non-enteric dosage form.

2. The method of claim 1, wherein the total deliverable dosage of ethyl oleate to said subject is from about 0.04 g per kg body weight to about 1.0 g per kg body weight.

3. The method of claim 2 wherein the administration of said composition to said subject replaces one or more of said subject's primary daily meal or meals.

4. The method of claim 3 wherein the composition may be administered to said subjects in single and plurality of doses or servings daily over the course of a weight management program.

5. The method of claim 2 wherein the administration of said composition to said subject is concomitant with consumption of food by said subject.

6. The method of claim 5 wherein said composition is administered from about 30 minutes to about 6 hours prior to consumption of food by said subjects.

7. The method of claim 6 wherein the composition is administered prior to consuming food, said food having a maximum triacylglycerol level of about 5 grams.

8. The method of claim 5 wherein the composition may be administered to said subjects in single and plurality of doses or servings daily over the course of a weight management program.

9. The method of claim 1 wherein the subject is a companion animal.

10. A method for controlling the appetite of a subject comprising administration of a composition comprising ethyl oleate, wherein ethyl oleate releases in the stomach; and wherein the composition is in a non-enteric dosage form.

11. The method of claim 10 wherein the administration of said composition to said subject replaces one or more of said subject's primary daily meal or meals.

12. The method of claim 1 wherein the non-enteric dosage form is selected from the group consisting of compressed and molded tablets, hard gelatin capsules, soft elastic gelatin capsules, and microcapsules that dissolve in the stomach, emulsions, suspensions, beverages, and solid food products.

13. The method of claim 1 wherein the composition further comprises a fatty acid.

14. The method of claim 13 wherein the fatty acid is selected from the group consisting of lauric acid, lauroleic acid, myristic acid, myristoleic acid, pentadecanoic acid, palmitic acid, palmitoleic acid, margaric acid, stearic acid, dihydroxystearic acid, oleic acid, ricinoleic acid, elaidic acid, linoleic acid, alpha-linolenic acid, dihomogamma-linolenic acid, eleostearic acid, licanic acid, arachidonic acid, arachidic acid, eicosenoic acid, eicosapentaenoic acid, behenic acid, erucic acid, docosahexaenoic acid, lignoceric acid and mixtures thereof.

15. The method of claim 14 wherein the fatty acid is selected from the group consisting of oleic acid, linoleic acid and mixtures thereof.

16. The method of claim 1 wherein the composition further comprises a second non-glyceryl fatty acid ester.

17. The method of claim 16 wherein the second non-glyceryl fatty acid ester is ethyl linoleate.

18. The method of claim 9 wherein the companion animal is a dog.

19. The method of claim 9 wherein the companion animal is a cat.

20. The method of claim 1 wherein the administration of said composition to said subject is concomitant with consumption of food by said subject.

21. The method of claim 20 wherein the food has a maximum triacylglycerol level of about 5 grams.

* * * * *